(12) United States Patent
Merz et al.

(10) Patent No.: US 9,517,081 B2
(45) Date of Patent: Dec. 13, 2016

(54) TOOL FOR A MEDICAL INSTRUMENT

(71) Applicant: Karl Storz GmbH & Co. KG, Tuttlingen (DE)

(72) Inventors: Robin Merz, Furtwangen (DE); Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 745 days.

(21) Appl. No.: 13/865,699

(22) Filed: Apr. 18, 2013

(65) Prior Publication Data

US 2013/0310865 A1 Nov. 21, 2013

(30) Foreign Application Priority Data

Apr. 18, 2012 (DE) .................. 10 2012 007 652

(51) Int. Cl.
| | |
|---|---|
| *A61B 17/32* | (2006.01) |
| *A61B 17/295* | (2006.01) |
| *A61B 17/29* | (2006.01) |
| *A61B 17/3209* | (2006.01) |
| *A61B 18/14* | (2006.01) |
| *A61B 17/00* | (2006.01) |
| *A61B 18/00* | (2006.01) |

(52) U.S. Cl.
CPC .............. *A61B 17/32* (2013.01); *A61B 17/29* (2013.01); *A61B 17/295* (2013.01); *A61B 17/3209* (2013.01); *A61B 18/1445* (2013.01); *A61B 2017/0046* (2013.01); *A61B 2017/2902* (2013.01); *A61B 2017/2931* (2013.01); *A61B 2018/00607* (2013.01); *A61B 2018/1455* (2013.01); *Y10T 29/49819* (2015.01)

(58) Field of Classification Search
CPC ... A61B 17/295; A61B 17/32; A61B 18/1455; A61B 2017/2902; A61B 2017/2931; A61B 2017/2903; A61B 2017/2912–2017/2917; A61B 2017/292; A61B 5/1411; A61B 5/150374; A61B 5/150381; A61B 5/150412; A61B 5/150442; A61B 5/150885; A61B 5/150908; A61B 5/151146; A61B 5/15186; A61B 5/15188; A61B 5/1519; A61B 5/15192; A61B 5/15196
USPC ................ 30/162; 606/170, 50–52, 205–208
See application file for complete search history.

(56) References Cited

U.S. PATENT DOCUMENTS

| | | |
|---|---|---|
| 5,389,098 A | 2/1995 | Tsuruta et al. |
| 5,554,164 A | 9/1996 | Wilson et al. |

(Continued)

FOREIGN PATENT DOCUMENTS

| | | |
|---|---|---|
| DE | 69633101 T2 | 8/2005 |
| EP | 2316367 A1 | 5/2011 |
| WO | 2008040486 A2 | 4/2008 |

*Primary Examiner* — Todd E Manahan
*Assistant Examiner* — Erich Herbermann
(74) *Attorney, Agent, or Firm* — Whitmyer IP Group LLC

(57) ABSTRACT

A tool for a medical instrument includes an effecting device, a transmission rod, of which the distal end is coupled to the effecting device, for transferring at least either a force or a torque to the effecting device, and a cutting device, which, to cut tissue, is movable in a channel in the transmission rod and in the effecting device. To cut tissue, the cutting device is movable in a channel in the transmission rod and in the effecting device.

20 Claims, 4 Drawing Sheets

(56) References Cited

U.S. PATENT DOCUMENTS

| | | | |
|---|---|---|---|
| 5,893,875 A * | 4/1999 | O'Connor | A61B 17/29 606/167 |
| 6,024,741 A | 2/2000 | Williamson, IV et al. | |
| 6,620,161 B2 | 9/2003 | Schulze et al. | |
| 7,744,615 B2 * | 6/2010 | Couture | A61B 18/1442 606/171 |
| 2002/0099372 A1 * | 7/2002 | Schulze | A61B 17/00008 606/51 |
| 2006/0226195 A1 | 10/2006 | Scirica et al. | |
| 2011/0060333 A1 | 3/2011 | Mueller | |
| 2011/0276084 A1 * | 11/2011 | Shelton, IV | A61B 17/29 606/205 |
| 2013/0085516 A1 * | 4/2013 | Kerr | A61B 18/1442 606/167 |

\* cited by examiner

TOOL FOR A MEDICAL INSTRUMENT

FIELD OF THE INVENTION

The present invention is based on a tool for a medical instrument and on a method for disassembling a tool.

BACKGROUND OF THE INVENTION

The expectations of medical instruments, in particular of medical instruments for microinvasive interventions, increase continuously. A variety of medical instruments comprising a tool with gripping or cutting function at the distal end are already offered and are widespread. Medical devices and medical staff prefer medical instruments that can be used in the most versatile manner possible. The more versatile the manner in which the individual medical instrument can be used, the smaller is the variety of the instruments to be kept ready. Medical instruments that can be used in a versatile manner can therefore reduce the capital outlay necessary in a medical device, even with higher unit costs. Due to a small variety and a low unit number of the medical instruments to be kept ready, the costs for storing and logistics can also be reduced. In the case of microinvasive medical instruments or medical instruments for microinvasive interventions, instruments also have to be exchanged less frequently during an intervention the more versatile the manner in which the individual instrument can be used.

SUMMARY OF THE INVENTION

The object of the present invention is to create an improved tool for a medical instrument, an improved medical instrument, and an improved method for disassembling a tool for a medical instrument.

This object is achieved by the subjects of the independent claims.

Developments are disclosed in the dependent claims.

A tool for a medical instrument comprises an effecting device, a transfer rod, of which the distal end is coupled to the effecting device, for transferring at least either a force or a torque to the effecting device, and a cutting device, which, to cut tissue, is movable in a channel in the transmission rod and in the effecting device.

The tool is provided and designed in particular for a microinvasive surgical instrument. The effecting device is in particular a pair of pincers with a plurality of mouth parts, of which at least one is movable, for gripping or squeezing tissue. Alternatively or in addition, the effecting device may have an electrosurgical function. In electrosurgery or in the case of electrosurgical measures, heat is generated in the tissue by means of a current flow and due to the electrical resistance of tissue (Joule's law). The current flow is localized as accurately as possible due to the shape and arrangement of the electrodes used in this instance. The tissue through which current has flowed is cauterized or destroyed by the heat produced. Tissue can thus be stuck together or closed for example, and hemorrhages stopped. Generally, high-frequency alternating currents are used in electrosurgery in order to avoid a stimulation of nerves and other undesired side effects. The terms "electrosurgery" and "HF surgery" are often used synonymously. A further term, often used synonymously, is electrocauterization.

The effecting device and the cutting device are two non-identical devices that in particular are designed to act in different ways on tissue and therefore have different features and components, at least in part. Even if the effecting device is a gripping device for example which is designed to hold tissue during a cutting operation by means of the cutting device, the effecting device and the cutting device have two potentially mutually supplementing, yet different, functions. In particular, the cutting device and the effecting device have no common components. The cutting device can be designed as a completely independent component that can be separated without destruction from the effecting device. The effecting device is in particular designed to have and to exert its provided function and action even in the absence of the cutting device.

The tool is in particular designed for releasable mechanical connection to a distal end of an outer shaft. The transmission rod is in particular designed for arrangement in the outer shaft. The transmission rod can be straight or curved, rigid or flexible. If the tool is provided and designed to be combined with a curved or flexible outer shaft to form a medical instrument, the transmission rod is flexible or resilient in particular at least in curved or curvable regions of the outer shaft. The proximal end of the transmission rod is in particular designed for coupling to a handling device, in particular to a lever or another actuation device on a handling device.

The channel in which the cutting device is movable extends in particular in the longitudinal direction of the tool. The longitudinal direction of the tool is in particular identical to the longitudinal direction of a distal end of an outer shaft when the tool is connected to the outer shaft. The channel extends in particular substantially as far as the distal end of the effecting device. For example in the case of an effecting device designed as a gripping device comprising two mouth parts, the channel extends preferably over the majority (in particular at least 80%) of the length of the mouth parts.

A tool having the described features can be used in a particularly versatile manner. For example, it can be used both to grip, prepare and coagulate tissue by means of the effecting device and also to subsequently sever the tissue by means of the cutting device. This makes it possible to perform complex medical interventions without exchanging the medical instrument or with less frequent exchanges of the medical instrument in the event of an intervention.

In the case of a tool as is described here, the transmission rod is coupled in particular to a pivotable mouth part of the tool.

In particular, the distal of the transmission rod is coupled to one, two or more pivotable mouth parts of the tool in such a way that a movement of the transmission rod in the longitudinal direction thereof or in the longitudinal direction of an outer shaft, to which the tool is mechanically connected, is accompanied by a pivoting of the pivotable mouth part(s) about pivot axes perpendicular to the longitudinal axis.

In the case of a tool as is described here, the effecting device in particular comprises two or more mouth parts electrically insulated from one another, wherein a first of the mouth parts is electrically conductively connected to the transfer rod, and wherein a second of the mouth parts is electrically conductively connected or connectable to an outer shaft.

With two or more mouth parts electrically insulated from one another, a use as a bipolar electrosurgical instrument is possible, with which a high-frequency alternating current for coagulating or cauterizing tissue flows almost exclusively in the small and comparatively well-defined space between the mouth parts. The tool can therefore be used for example initially to electrosurgically close a vessel or another hollow organ and immediately thereafter to sever said vessel or other hollow organ.

In the case of a tool as is described here, the cutting device in particular is designed to cut with a movement in the direction parallel to the longitudinal axis of the tool.

In particular, the cutting device comprises at its distal end an at least partly distally directed (in particular not parallel to the longitudinal axis and to the provided direction of movement) blade. By displacing the cutting device from a proximal position to a distal position, tissue can be cut or severed and is held for example by means of the effecting device.

In the case of a tool as is described here, the channel in particular comprises a groove in the transfer rod, wherein at least either the cutting device or the groove is designed such that a movement of the cutting device in proximal direction accompanies a lifting out of the cutting device from the groove.

In particular, the cutting device and the groove are designed such that the proximal end of the cutting device is lifted out from the groove when it approaches the proximal end of the groove or reaches the proximal end of the groove. This may enable a removal of the cutting device from the groove by means of a simple movement of the cutting device in proximal direction.

In the case of a tool as is described here, the channel in particular comprises a groove, in particular a groove in the transfer rod, wherein the groove has a continuously reducing depth in proximal direction in a region close to the proximal end of the groove.

In particular, the bottom or the base of the groove is ramp-shaped with a constant or varying incline.

Alternatively or in addition, the cutting device comprises at its proximal end a ramp-shaped region, which can slide over the edge of the groove at the proximal end thereof, wherein a movement of the cutting device in proximal direction accompanies a lifting out of the cutting device from the groove.

A tool as is described here in particular comprises a coupling device for releasable mechanical connection of the tool to a distal end of an outer shaft, wherein, in all positions provided for the cutting device during the use of the tool, the proximal end of the cutting device is arranged proximally of the coupling device and the distal end of the cutting device is arranged distally of the coupling device.

The cutting device in particular comprises a coupling device for releasable mechanical connection of the cutting device to a distal end of an inner shaft or a transfer device. The arrangement of the proximal end of the cutting device and of its coupling device proximally of the coupling device provided for releasable mechanical connection of the tool to an outer shaft can be advantageous in terms of the required and available installation space and therefore in terms of the design and manufacturing effort and of the degree of miniaturization achievable.

The cutting device is in particular formed in one piece, and for example is produced from a single piece of metal.

In the case of a tool as is described here, the cutting device in particular comprises a bar-shaped region between its proximal end and its distal end.

The bar-shaped region of the cutting device in particular has a rectangular cross section and in particular is designed to be arranged completely within the channel. The bar-shaped region is in particular arranged completely within the aforementioned groove in the transmission rod with the provided use and arrangement of the cutting device, that is to say does not protrude or does not protrude considerably beyond the edges of the groove.

In the case of a tool as is described here, the cutting device in particular comprises a protrusion, which protrudes in a direction perpendicular to the provided direction of movement of the cutting device.

The protrusion is in particular arranged at or close to the proximal end of the cutting device and in particular defines the proximal end of the aforementioned bar-shaped region of the cutting device since the protrusion constitutes a deviation from the bar-shaped design. With an arrangement of the cutting device in the aforementioned groove in the transfer rod, merely the protrusion protrudes from the groove and forms a coupling device for releasable, in particular interlocked, mechanical connection of the cutting device to a distal end of an inner shaft or another transfer device. Furthermore, the protrusion when disassembling the tool can be used to shift the cutting device manually in the proximal direction in order to lift it out from the groove, as described above.

In the case of a tool as is described here, the cutting device is in particular arranged completely in the channel, apart from the protrusion, in a position provided during the use of the tool.

A medical instrument comprises a tool as is described here and an inner shaft, of which the distal end is releasably mechanically connectable to the cutting device.

In the case of a medical instrument as is described here, the inner shaft in particular at its distal end comprises an L-shaped slit or an L-shaped groove for receiving the protrusion on the cutting device.

The L-shaped slit or the L-shaped groove at the distal end of the inner shaft on the one hand and the protrusion on the cutting device on the other hand form corresponding bayonet coupling devices. The inner shaft can therefore be coupled or mechanically connected to the cutting device by means of an axial and a subsequent rotary movement relative to the tool and the transfer rod, and can be separated again from said cutting device by means of a reversed relative movement.

In the case of a method for disassembling a tool for a medical instrument, wherein the tool comprises an effecting device and a cutting device in a channel, a mechanical connection between a distal end of a transfer device and the cutting device is separated and the cutting device is moved in proximal direction relative to the tool, wherein the cutting device is lifted out from the channel.

The method is applicable in particular to a tool having the features described here. The mechanical connection between the distal end of the transfer device and the cutting device (in particular the proximal end of the cutting device) is achieved without destruction or reversibly. To this end, the distal end of the transfer device and the cutting device (in particular the proximal end of the cutting device) comprise coupling devices corresponding to one another.

When the cutting device is moved in proximal direction, the at least partial lifting out of the cutting device from the channel occurs automatically or independently due to features of the cutting device and/or the channel. When the cutting device is lifted out from the channel, in particular the proximal end of the cutting device is lifted out of a groove in a transfer rod. In so doing, in particular the proximal end of the cutting device slides over a ramp-shaped region at the proximal end of the groove and/or a ramp-shaped region at the proximal end of the cutting device at a proximal edge of the groove.

In order to move the cutting device, the proximal end of the cutting device, in particular the aforementioned protrusion, can be gripped manually or by means of an aid. For example, a finger is pressed onto the protrusion and the protrusion is driven in proximal direction by a movement of the finger due to interlocked and/or force-locked engagement.

The method described here for disassembling a tool can be useful in the event of post-processing after use of a medical instrument comprising the tool and in the event of preparation for the cleaning and sterilizing of the tool and therefore also for the preparation of a further use within the scope of a diagnostic, surgical or therapeutic procedure. The method for disassembly however does not itself constitute a diagnostic, surgical or therapeutic method.

In the case of a method as is described here, a distal end of an outer shaft is separated from the tool, in particular before the separation of the mechanical connection between the distal end of the transfer device and the cutting device.

BRIEF DESCRIPTION OF THE DRAWINGS

Embodiments will be explained in greater detail hereinafter on the basis of the accompanying figures, in which.

DETAILED DESCRIPTION OF THE INVENTION

Figure 1:
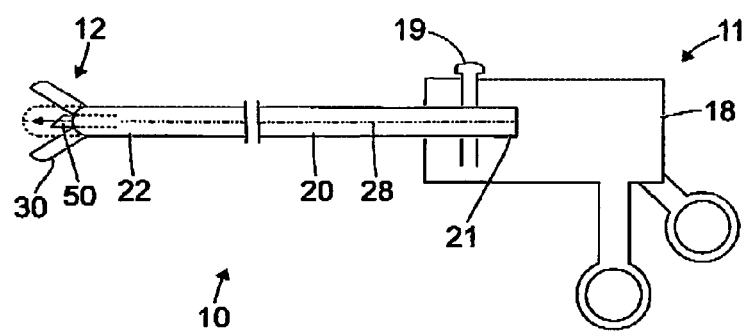
FIG. 1 shows a schematic illustration of a medical instrument.

FIG. 1 shows a schematic illustration of a medical instrument 10 having a proximal end 11 and a distal end 12. At the proximal end 11, the medical instrument 10 comprises a handling device 18, which is designed to be grasped by the hand of medical staff and to receive manually generated forces and torques. To this end, the handling device 18 in particular comprises a plurality of grip parts, which are movable at least in part relative to one another.

A shaft 20 extends from the proximal end 11 or the handling device 18 to the distal end 12 of the medical instrument 10. The shaft 20 comprises a proximal end 21 and a distal end 22. The proximal end 21 of the shaft 20 is mechanically connected to the handling device 18, in particular is arranged in a recess having a shaping corresponding to the proximal end 21 of the shaft 20, where it is locked in an interlocking manner by means of a locking device 19.

The shaft 20 comprises a longitudinal axis 28. In the case of a circular cylindrical shaping of the shaft 20, the longitudinal axis 28 in particular is the axis of symmetry of the lateral surface of the shaft 20. The inner structure of the shaft 20 described below can be rotationally symmetrical about the longitudinal axis 28. The shaft 20 can be straight or, by contrast with the illustration in FIG. 1, curved, rigid or flexible. If the shaft 20 is curved or flexible at least in some portions, the longitudinal axis hereinafter means the longitudinal axis of the shaft 20 at its proximal end 21 or at its distal end 22. The shaft 20 is in particular also rotatable about its longitudinal axis 28 in the state locked in the handling device 18.

The distal end 22 of the shaft 20 is connected to a tool, which comprises a gripping device 30 and a cutting device 50. The gripping device 30 in particular comprises two gripping jaws, of which at least one is pivotable about a pivot axis perpendicular to the drawing plane of FIG. 1. In the example shown in FIG. 1, both gripping jaws are pivotable between open positions, which are illustrated in FIG. 1 by solid lines, and closed positions, which are illustrated in FIG. 1 by dashed lines. As indicated in FIG. 1 by an arrow, the cutting device 50 is movable in a direction parallel to the longitudinal axis 28, more specifically both when the mouth parts of the gripping device adopt their open positions and when they adopt their closed positions.

Exemplary embodiments of the tool 30, 50 and its releasable mechanical connection to an outer shaft, an inner shaft and a transmission rod are presented hereinafter. The tools, outer shafts, inner shafts and transfer rods presented hereinafter may be designed and used to form a medical instrument having the features illustrated with reference to FIG. 1 and/or having other features.

Figure 2:
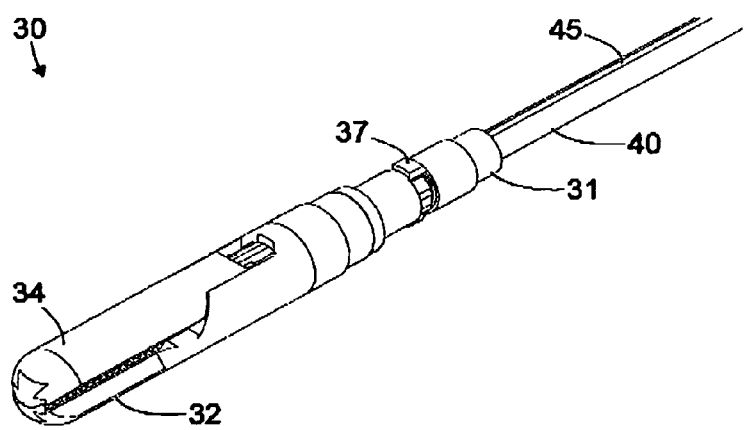
FIG. 2 shows a schematic axonometric illustration of a gripping device for a medical instrument.

FIG. 2 shows a schematic axonometric illustration of a gripping device 30, which is provided and designed to form a medical instrument as is presented above with reference to FIG. 1. The gripping device 30 comprises a proximal end 31 and two mouth parts 32, 34, which form the distal end of the gripping device 30. In contrast to the gripping device indicated in FIG. 1, the gripping device 30 illustrated in FIG. 2 comprises a stationary mouth part 32 and a pivotable mouth part 34. Close to the proximal end 31, the gripping device 30 comprises two symmetrically arranged bayonet claws or catches 37, of which one is arranged on a side facing away from the viewer and therefore is largely obscured.

The gripping device 30 is mechanically connected to a transmission rod 40. The transmission rod 40 is movable relative to the gripping device 30, in particular relative to the proximal end 31 and to the stationary mouth part 32 in the axial direction, that is to say parallel to the longitudinal axis of the transmission rod 40 and to the longitudinal axis 28 of the shaft 20 (see FIG. 1), within a predetermined interval. The distal end of the transmission rod 40 arranged within the gripping device 30 and therefore not visible in FIG. 2 is coupled to the pivotable mouth part 34 in such a way that an axial movement of the transmission rod 40 accompanies a pivoting movement of the pivotable mouth part 34. In the transmission rod 40, a groove 45 is provided, which in particular has a narrow and deep rectangular cross section. The groove 45 in the transmission rod 40 is continued at the distal end thereof (not visible in FIG. 2) by a cross section corresponding to a channel and extending between the mouth parts 32, 34 almost as far as the distal ends thereof.

Parts of the gripping device 30, in particular the catches 37 and also the transmission rod 40 are manufactured from stainless steel or another metal. The catches 37 and the transmission rod 40 are electrically insulated from one another. The mouth parts 32, 34 comprise metal and therefore electrically conductive grip areas, which are electrically insulated from one another when they do not bear against one another, as shown in FIG. 2. The catches 37 and the transmission rod 40 are each electrically conductively connected to the grip area of a mouthpart 32, 34. In particular, the catches 37 are electrically conductively connected to the grip area of the fixed mouth part 32, and the transmission rod 40 is electrically conductively connected to the grip area of the pivotable mouth part 34.

Figure 3:
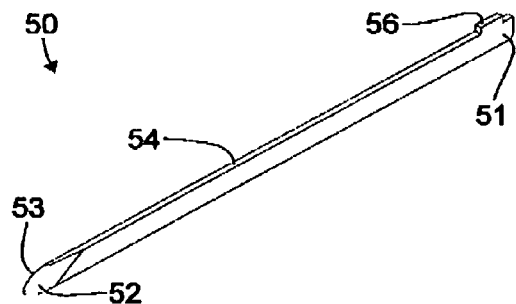
FIG. 3 shows a schematic axonometric illustration of a cutting device.

FIG. 3 shows a schematic axonometric illustration of a cutting device 50 having a proximal end 51 and a distal end 52. At the distal end 52, the cutting device 50 comprises a blade 53. At the proximal end, the cutting device 50 comprises a protrusion 56. Between the proximal end 51 and the distal end 52, the cutting device comprises a bar-shaped region 54, which basically has the form of a strip-shaped plate or of a bar with a rectangular cross section.

Between the protrusion 56 at the proximal end 51 and the blade 53 at the distal end 52, the cross section of the cutting device 50 corresponds substantially to the cross section of the groove 45 in the transmission rod 40 (see FIG. 2), and therefore the cutting device 50, apart from the protrusion 56, can be received completely by the groove 45 in the transmission rod 40 and can be guided therein with little play and little friction and can be displaceable in the longitudinal direction of the transmission rod 40 and of the cutting device 50. The protrusion 56 is provided to protrude from the groove 45 in the transmission rod 40.

Figure 4:
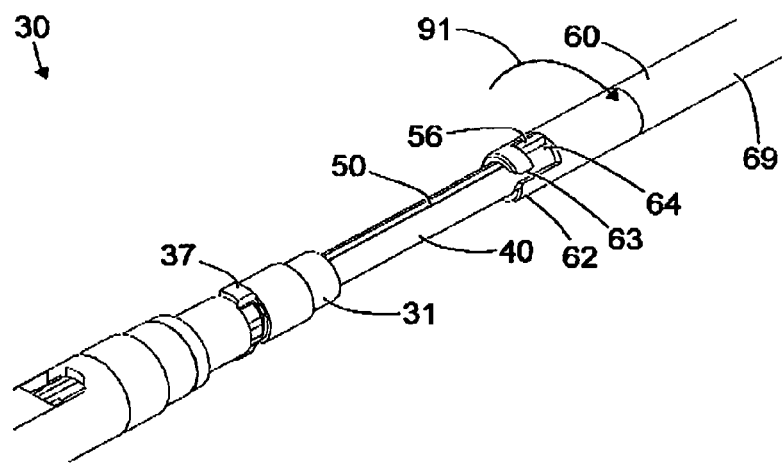
FIG. 4 shows a further schematic axonometric illustration of the devices from FIGS. 2 and 3.

FIG. 4 shows a further schematic axonometric illustration of the gripping device from FIG. 2 and of the cutting device 50 from FIG. 3. In the illustration in FIG. 4, the cutting device 50 is arranged in the groove 45 in the transmission rod 40 (see FIG. 2). The distal end 52 of the cutting device 50 (see FIG. 3) is arranged here in the gripping device and in particular between the mouth parts 32, 34. The protrusion 56 protrudes from the groove 45.

In FIG. 4, an inner shaft 60 is also shown, which has substantially a tubular or circular cylindrical shaping. At its distal end 62, the inner shaft 60 comprises an L-shaped slit with an axial portion 63 or a portion 63 extending in the axial direction and a circumferential portion 64 or a portion 64 extending in the circumferential direction. The width of the axial portion 63 to be measured in the circumferential direction and the width of the circumferential portion 64 of the L-shaped slit to be measured in the axial direction are matched to the dimensions of the protrusion 56 on the cutting device 50.

Once the transmission rod 40 has been introduced into the inner shaft 60, the protrusion 56 can be introduced through the axial portion 63 until in the circumferential portion 64 by means of a relative movement in the axial direction. When the protrusion 56 on the cutting device 50 is located in the circumferential portion 64 of the L-shaped slit at the distal end 62 of the inner shaft 60, the inner shaft 60 can be rotated relative to the gripping device 30, the transmission rod 40 and the cutting device 50 in a first direction 91 until the configuration shown in FIG. 4 has been reached.

In the relative positioning of the cutting device 50 and inner shaft 60 shown in FIG. 4, the cutting device 50 and inner shaft 60 are coupled rigidly to one another (apart from play) in terms of axial movements. An axial movement of the inner shaft 60 therefore accompanies a corresponding axial movement of the cutting device 50. A movement of the blade 53 at the distal end 52 of the cutting device 50 (see FIG. 3) in the aforementioned channel (not visible in the figures) between the mouth parts 32, 34 can therefore be implemented by means of the inner shaft 60, for example in order to sever tissue gripped by the mouth parts 32, 34 after an electrocauterization procedure.

The inner shaft 60 comprises an insulating sheath 69, of which the distal edge is arranged close to the L-shaped slit 63, 64, and which may extend until close to the proximal end of the inner shaft 60.

Figure 5:
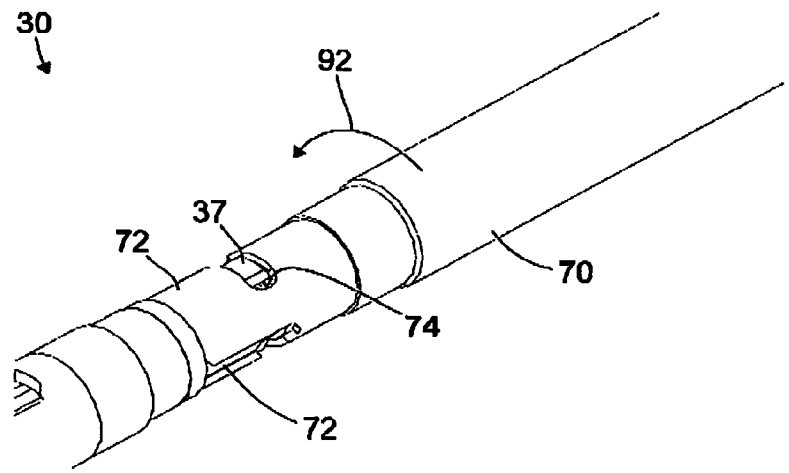
FIG. 5 shows a further schematic axonometric illustration of the devices from FIGS. 2 to 4.

FIG. 5 shows a further schematic axonometric illustration of the gripping device 30 from FIGS. 2 and 4. The illustration in FIG. 5 differs from the illustration in FIGS. 2 and 4 in that an outer shaft 70 is coupled to the gripping device 30. The outer shaft 70 comprises at its distal end 72 two symmetrically arranged L-shaped slits, each having an axial portion 73 and a circumferential portion 74. One of the L-shaped slits is arranged on a side of the outer shaft 70 facing away from the viewer and therefore is not visible in FIG. 5.

The width of the axial portions 73 to be measured in the circumferential direction and the width of the circumferential portions 74 of the L-shaped slits to be measured in the axial direction are matched to the dimensions of the catches 37 on the gripping device 30. As a result of a movement of the outer shaft 70 in the axial direction and a subsequent rotation relative to the gripping device 30, the catches 37 can be introduced through the axial portions 73 into the circumferential portions 74 until the configuration shown in FIG. 5 has been reached. In the configuration or arrangement shown in FIG. 5 of the catches 37 in the circumferential portions 74 of the L-shaped slits at the distal end 72 of the outer shaft 70, the outer shaft 70 and the gripping device 30 are rigidly coupled to one another (apart from play) with regard to axial forces and movements.

By comparison of FIGS. 4 and 5, it can be seen that the circumferential portions 64, 74 of the L-shaped slits at the distal ends 62, 72 of the inner shaft 60 on the one hand and of the outer shaft 70 on the other hand extend in opposite directions from the axial portions 63, 73. Accordingly, the direction 92 in which the outer shaft 70 is to be rotated relative to the gripping device 30 in order to reach the coupled configuration shown in FIG. 5 is opposite to the direction 91 in which the inner shaft 60 is to be rotated relative to the gripping device 30 and relative to the cutting device 50 in order to reach the coupled configuration shown in FIG. 4.

Figure 6:
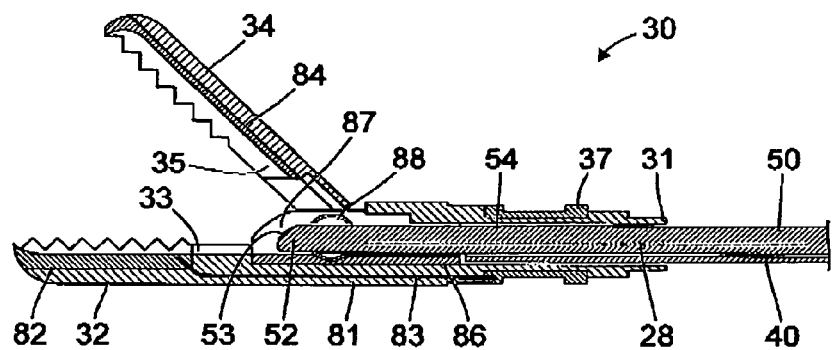
FIG. 6 shows a schematic sectional illustration of the tool from FIGS. 2, 4 and 5.

FIG. 6 shows a schematic sectional illustration of the tool from FIGS. 2, 4 and 5. The illustrated sectional plane contains the longitudinal axis 28 (see FIG. 1).

The gripping device 30 comprises a main body 81, which has an electrically insulating material and can be joined from a plurality of elements. The main body 81 extends from the proximal end 31 of the gripping device 30 to the proximal end thereof and in particular forms the stationary mouth part 32. The stationary mouth part 32 comprises a grip area insert 82 made of metal. The catches 37 are components of a sleeve-shaped metal component that is connected to the grip area insert 82 on the stationary mouth part 32 by means of a wire arranged at least in part in the main body 81 of the gripping device 30 or by means of another electrically conductive connection 83.

The pivotable mouth part 34 has a metal grip area insert 84. In the main body 81, a metal bearing component 86 is arranged, which is electrically insulated from the catches 37 and the grip area insert 82 of the stationary mouthpart 32 by means of the main body 81. A journal 88 is rigidly connected to the pivotable mouth part 34 and is mounted in the bearing component 86 so as to be rotatable about a pivot axis perpendicular to the sectional plane in FIG. 6. The journal 88 and a web-shaped or plate-shaped region of the bearing component 86, said region being arranged parallel to the sectional plane in FIG. 6, are arranged behind the sectional plane in FIG. 6 as considered by the viewer. Symmetrically about the sectional plane in FIG. 6, a further journal is arranged on the pivotable mouth part 34 and a further plate-shaped region of the bearing component 86, in which the further journal is mounted, is arranged before the sectional plane of FIG. 6 or between the sectional plane and the viewer. The bearing component 86 and the journal 88 define the pivot axis of the pivotable mouth part 34, said pivot axis being arranged perpendicular to the sectional plane of FIG. 6. The journals 88 are electrically conductively connected to the grip area insert 84 on the pivotable mouth part 34. In particular, the journals 88 are each formed in one piece with a strut extending parallel to the pivotable mouth part 34, wherein the struts and the grip area insert 84 are welded, soldered, screwed or otherwise joined.

The transmission rod 40 protrudes from the proximal end 31 of the gripping device 30 into the main body 81. The transmission rod 40 is mechanically coupled to the pivotable mouth part 34 in such a way (not visible in FIG. 6) that a movement in translation of the transmission rod 40 parallel to the longitudinal axis 28 accompanies a pivoting movement of the pivotable mouth part 34 about the pivot axis, defined by the journal 88, perpendicular to the sectional plane of FIG. 6. In the distal position of the transmission rod 40 shown in FIG. 6, the pivotable mouth part 34 adopts an open position or a position distanced from the stationary mouth part 32.

The transmission rod 40 formed from a metal material is electrically conductively connected to the journal 88 and the grip area insert 84 on the pivotable mouth part 34. The transmission rod 40 is electrically insulated by the main body 81 of the gripping device 30 from the catches 37 and from the grip area insert 82 of the stationary mouth part 32.

Figure 8:
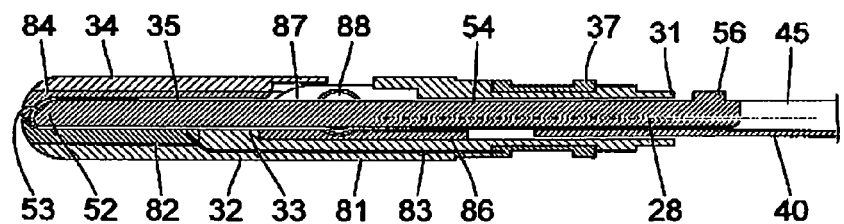
FIG. 8 shows a further schematic sectional illustration of the tool from FIGS. 2 and 4 to 7.
Figure 9:
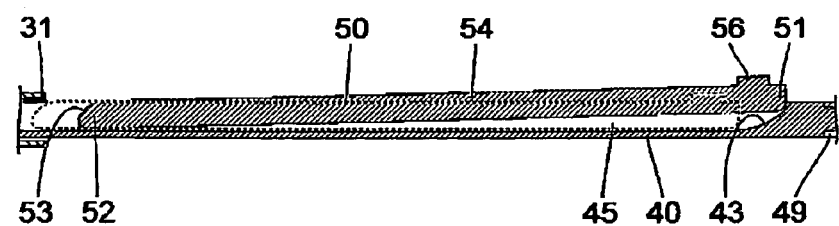
FIG. 9 shows a further schematic sectional illustration of the tool from FIGS. 2 and 4 to 8.

The cutting device 50 is arranged in a groove in the transmission rod 40, which is only provided with a reference sign in FIGS. 8 and 9, and in a groove 87 in the bearing component 86. The groove 87 in the bearing component 86 is defined in a direction perpendicular to the sectional plane in FIG. 6 by the aforementioned plate-shaped regions of the bearing component 86, in which the journals 88 of the pivotable mouth part 34 are mounted, or is formed by the gap between the two plate-shaped components. In an extension of the groove in the transmission rod 40 and of the groove 87 in the bearing component 86 in the distal direction, a groove 33 is provided in the stationary mouth part 32, in particular in the grip area insert 82 of the stationary mouth part 32, and a groove 35 is provided in the pivotable mouth part 34, in particular in the grip area insert 84 of the pivotable mouthpart 34.

Cross sections of electrically conductive components, in particular of the catches 37, the transmission rod 40, the cutting device 50, the grip area inserts 82, 84 and the bearing component 86, are illustrated in FIG. 6 by dense hatching. Cross sections of electrically insulating components, in particular of the main body 81, are illustrated by wide hatchings. As already mentioned, an electrically conductive connection exists between the transmission rod 40 and the grip area insert 84 on the pivotable mouth part 34 via the journals 88 and the aforementioned struts, and an electrically conductive connection 83 exists between the catches 37 and the grip area insert 82 on the stationary mouth part 32. The catches 37 and the grip area insert 84 on the pivotable mouth part 34 are electrically insulated from the transmission rod 40 and the grip area insert 82 on the stationary mouth part 32, provided the grip area inserts 82, 84 do not contact one another. The gripping device 30 can therefore be used as a bipolar electrosurgical instrument, wherein one pole or one potential is fed via the transmission rod 40 and the other pole or the other potential is fed via an outer shaft and the catches 37.

Figure 7:
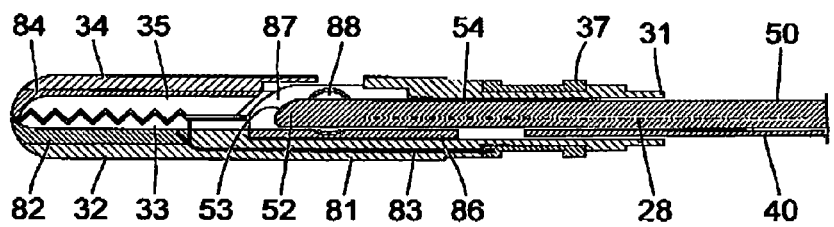
FIG. 7 shows a further schematic sectional illustration of the tool from FIGS. 2 and 4 to 6.

FIG. 7 shows a further schematic sectional illustration of the gripping device 30 form FIGS. 2 and 4 to 6. The sectional plane of FIG. 7 corresponds to the sectional planes in FIG. 6. In FIG. 7, the transmission rod 40 is shown in a proximal position, and the pivotable mouth part 34 is shown in a corresponding closed position or in a position bearing against the stationary mouth part 32. In FIG. 7, tissue (not shown) between the mouth parts 32, 34 can be coagulated or cauterized by means of a current flow between the grip area inserts 82, 84.

It can be seen in FIG. 7 that the grooves 33, 35 in the mouth parts 32, 34 form an extension of the groove in the transmission rod 40 and of the groove 87 in the bearing component 86 in the distal direction. The groove in the transmission rod 40, the groove 87 in the bearing component 86, and the grooves 33, 35 in the mouth parts 32, 34 form a channel, in which the cutting device 50 is guided with little play and little friction and is movable or displaceable between a proximal position (in particular the position shown in FIGS. 6 and 7) and a distal position. To this end, in particular the groove in the transmission rod 40, the groove 87 in the bearing component 86, and the grooves 33, 35 in the mouth parts 32, 34 have cross sections (in sectional planes perpendicular to the sectional planes of FIGS. 6 and 7 and perpendicular to the longitudinal axis 28) that correspond to the cross section of the cutting device 50, in particular of the bar-shaped region 54 thereof, or that are only slightly larger than said cross section of the cutting device.

FIG. 8 shows a further schematic sectional illustration of the gripping device 30 from FIGS. 2 and 4 to 7. The sectional plane of FIG. 8 corresponds to the sectional planes of FIGS. 6 and 7. As in FIG. 7, the transmission rod 40 in FIG. 8 is also shown in a proximal position and the pivotable mouth part 34 is also shown in a closed position.

In FIG. 8, the cutting device 50 is shown in a distal position. The groove 45 in the transmission rod 40 is thus visible proximally of the cutting device 50. In the distal position of the cutting device 50 shown in FIG. 8, said cutting device fills the grooves 33, 35 in the mouth parts 32, 34 almost completely. The blade 53 on the cutting device 50 is located directly proximally of the distal ends of the mouth parts 32, 34. When the cutting device is moved from the proximal position shown in FIG. 7 to the distal position shown in FIG. 8, the blade 53 of the cutting device 50 severs tissue (not illustrated in the figures) between the mouth parts 32, 34, in particular after electrocauterization of the tissue.

At the proximal end 51 of the cutting device 50, the protrusion 56 also illustrated in FIGS. 3 and 4 is visible and can be releasably coupled in an interlocking manner to the distal end 62 of an inner shaft 60 (see FIG. 4) and enables a movement of the cutting device 50 between the positions shown in FIGS. 7 and 8 by means of the inner shaft 60.

FIG. 9 shows a further schematic sectional illustration, of which the sectional plane corresponds to the sectional planes in FIGS. 6 to 8. The detail shown in FIG. 9 is shifted in proximal direction compared to the detail shown in FIGS. 6 to 8. The proximal end 31 of the gripping device 30 (see FIGS. 6 to 8) is visible at the distal (left-hand) edge of the image. An insulating sheath 49 on the transmission rod 40 is visible at the proximal (right-hand) edge of the image.

The groove 45 in the transmission rod 40 comprises at its proximal end a ramp-shaped region 43 with an increasing incline. In the ramp-shaped region 43, the depth of the groove decreases continuously or steadily. The cutting device 50 is illustrated twice in FIG. 9. The position of the cutting device 50 illustrated merely by dashed contours is arranged proximally far of the position illustrated in FIGS. 6 and 7, but completely within the groove 45 in the transmission rod 40 apart from the protrusion 56. If the cutting device 50 is shifted further in proximal direction, the cutting device 50 adopts the position illustrated in FIG. 9 in solid lines. In this position, the proximal end 51 of the cutting device 50 is lifted out partially from the groove 45 due to the ramp-shaped region 43 at the proximal end of the groove 45.

The cutting device 50 can therefore be lifted out from the groove 45 and then removed therefrom by merely displacing the cutting device 50 (for example by means of a corresponding application of force of a finger on the protrusion 56). Since, here, the proximal end 51 of the cutting device 50 is initially lifted out from the groove and the cutting device can then be grasped at the proximal end 51, the risk of damage to the blade 53 is low.

Figure 10:
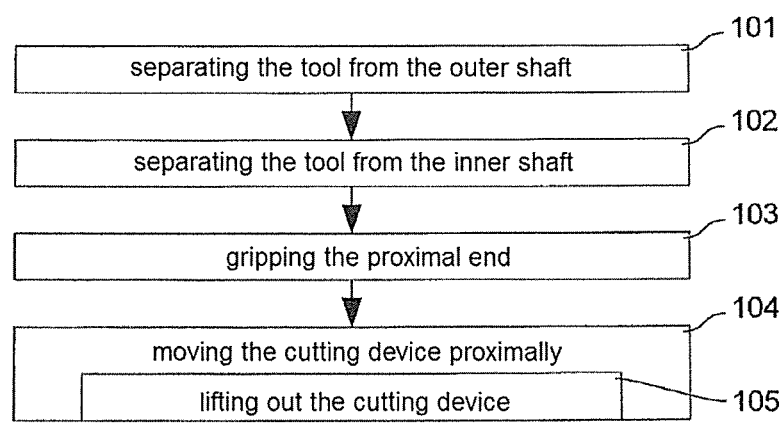
FIG. 10 shows a schematic flow diagram of a method for disassembling a tool.

FIG. 10 shows a schematic flow diagram of a method for disassembling a tool for a medical instrument. The method can be carried out in particular on a tool having the features presented above with reference to FIGS. 1 to 9, but can also be applied to tools having other features. To simplify comprehension, reference signs from FIGS. 1 to 9 will be used hereinafter by way of example.

In a first step 101, the tool 30, 50 is separated or released from the distal end 72 of an outer shaft 70, in particular by releasing a bayonet coupling. In a second step 102, the tool 30, 50 is separated or released from a distal end 62 of an inner shaft 60 or another transfer device. Here, a mechanical connection between the distal end 62 of the transfer device 60 and a cutting device 50 is released in particular. In a third step 103, the proximal end 51 of the cutting device 50 is grasped. In a fourth step 104, the cutting device 50 is moved in proximal direction relative to other components of the tool. The third step 103 and the fourth step 104 are in particular carried out by placing a finger on the protrusion 56 on the cutting device 50, pressing against said protrusion and using the finger to slide the protrusion 56 and the cutting device 50 in proximal direction. As the cutting device 50 is moved in proximal direction 104, the cutting device 50 is lifted out from a groove 45 in a fifth step 105. This occurs in particular when the proximal end of the groove 45 is reached.

REFERENCE SIGNS 10 medical instrument
11 proximal end of the medical instrument 10
12 distal end of the medical instrument 10
18 handling device at the proximal end 11 of the medical instrument 10
19 locking device on the handling device 18
20 shaft of the medical instrument 10
21 proximal end of the shaft 20
22 distal end of the shaft 20
28 longitudinal axis of the shaft 20
30 gripping device at the distal end 12 of the medical instrument 10
31 proximal end of the gripping device 30
32 stationary mouth part of the gripping device 30
33 groove in the stationary mouth part 32 of the gripping device 30
34 pivotable mouth part of the gripping device 30
35 groove in the pivotable mouth part 34 of the gripping device 30
37 catch at the proximal end 31 of the gripping device 30
40 transmission rod of the medical instrument 10
43 ramp-shaped region at the proximal end of the groove 45
45 groove in the transmission rod 40
49 insulating sheath on the transmission rod 40
50 cutting device at the distal end 12 of the medical instrument 10
51 proximal end of the cutting device 50
52 distal end of the cutting device 50
53 blade on the cutting device 50
54 bar-shaped region of the cutting device 50
56 protrusion at the proximal end 51 of the cutting device 50
60 inner shaft of the medical instrument 10
62 distal end of the inner shaft 60
63 axial portion of an L-shaped slit at the distal end 62
64 circumferential portion of an L-shaped slit at the distal end 62
69 insulating sheath on the inner shaft 60
70 outer shaft of the medical instrument 10
72 distal end of the outer shaft 70
73 axial portion of an L-shaped slit at the distal end 72
74 circumferential portion of an L-shaped slit at the distal end 72
81 main body of the gripping device 30
82 grip area insert on the stationary mouth part 32
83 conductive connection between the catch 37 and grip area insert 82 on the stationary mouth part 32
84 grip area insert on the pivotable mouth part 34
86 bearing component
87 groove in the bearing component 86
88 journal on the pivotable mouth part 34
101 first step (separating the tool from the outer shaft)
102 second step (separating the tool from the inner shaft)
103 third step (gripping the cutting device)
104 fourth step (moving the cutting device in proximal direction)
105 fifth step (lifting out the cutting device)

The invention claimed is:

1. A tool for a medical instrument, comprising:
    an effecting device;
    a transmission rod movable relative to the effecting device, of which the distal end is coupled to the effecting device, for transmitting at least either a force or a torque to the effecting device;
    a cutting device, which, to cut tissue, is movable in a channel in the transmission rod and in the effecting device, the channel including a groove in the transmission rod;
    at least either the cutting device or the groove is designed such that a movement of the cutting device in a proximal direction accompanies a lifting out of the cutting device from the groove for removal from the tool.

2. The tool according to claim 1, wherein the cutting device is designed to cut with a movement in the direction parallel to the longitudinal axis of the tool.

3. The tool according to claim 1, wherein
    the groove has a continuously reducing depth in proximal direction in a region close to the proximal end of the groove.

4. The tool according to claim 1, further comprising:
    a coupling device for releasable mechanical connection of the tool to a distal end of an outer shaft, wherein, in all positions provided for the cutting device during the use of the tool, the proximal end of the cutting device is arranged proximally of the coupling device and the distal end of the cutting device is arranged distally of the coupling device.

5. The tool according to claim 1, wherein the cutting device comprises a bar-shaped region between its proximal end and its distal end.

6. The tool according to claim 1, wherein the cutting device comprises a protrusion, which protrudes in a direction perpendicular to the provided direction of movement of the cutting device.

7. The tool according to claim 6, wherein the cutting device is arranged completely in the channel, apart from the protrusion, in a position provided during the use of the tool.

8. A medical instrument, comprising:
a tool according to claim 1;
an inner shaft, of which the distal end is releasably mechanically connectable to the cutting device.

9. The medical instrument according to claim 8, wherein the inner shaft at its distal end comprises an L-shaped slit or an L-shaped groove for receiving a protrusion on the cutting device.

10. A method for disassembling a tool for a medical instrument, wherein the tool comprises:
an effecting device;
a transmission rod, of which the distal end is coupled to the effecting device, for transmitting at least either a force or a torque to the effecting device; and
a cutting device, which, to cut tissue, is movable in a channel in the transmission rod and in the effecting device, the channel including a groove in the transmission rod;
said method comprising the following steps:
separating a mechanical connection between a distal end of a transfer device and the cutting device;
moving the cutting device relative to the tool in the proximal direction, wherein at least either the cutting device or the groove is designed such that movement of the cutting device in the proximal direction accompanies a lifting out of the cutting device from the groove;
lifting out the cutting device from the tool.

11. The method according to claim 10, further comprising the following step:
separating a distal end of an outer shaft from the tool before separating the mechanical connection between the distal end of an inner shaft and the cutting device.

12. The method according to claim 10, wherein there is a ramp-shaped region at the proximal end of the groove for lifting the cutting device from the groove.

13. The method according to claim 10, wherein the cutting device is designed to cut with a movement in the direction parallel to the longitudinal axis of the tool.

14. The method according to claim 10, wherein:
a coupling device provides releasable mechanical connection of the tool to a distal end of an outer shaft, and
in all positions provided for the cutting device during the use of the tool, the proximal end of the cutting device is arranged proximally of the coupling device and the distal end of the cutting device is arranged distally of the coupling device.

15. The method according to claim 10, wherein the cutting device comprises a bar-shaped region between its proximal end and its distal end.

16. The method according to claim 10, wherein the cutting device comprises a protrusion, which protrudes in a direction perpendicular to the provided direction of movement of the cutting device.

17. The method according to claim 16, wherein the cutting device is arranged completely in the channel, apart from the protrusion, in a position provided during the use of the tool.

18. The method according to claim 16, wherein the cutting device is adapted so that it can be lifted out and removed from the groove by using a finger to slide the protrusion and the cutting device in the proximal direction.

19. The method according to claim 10, wherein:
the medical device has an inner shaft with a distal end releasably mechanically connectable to the cutting device.

20. The method according to claim 19, wherein the inner shaft at its distal end comprises an L-shaped slit or an L-shaped groove for receiving a protrusion on the cutting device.

* * * * *